United States Patent [19]

Mattson et al.

[11] Patent Number: 5,596,019
[45] Date of Patent: Jan. 21, 1997

[54] N-ACYL-CYCLOALKYLAMINE DERIVATIVES AS MELATONERGICS

[75] Inventors: Ronald J. Mattson, Meriden; Daniel J. Keavy, Middletown; Michael F. Parker, Somers; Graham Johnson, Madison, all of Conn.

[73] Assignee: Bristol-Myers Squibb Company, Princeton, N.J.

[21] Appl. No.: 487,306

[22] Filed: Jun. 7, 1995

[51] Int. Cl.$^6$ .......................... A61K 31/16; C07C 233/06
[52] U.S. Cl. .......................... 514/629; 514/625; 514/627; 514/595; 564/192; 564/204; 564/207; 564/217; 564/218; 564/47
[58] Field of Search ................ 514/625, 627, 514/629; 564/192, 204, 207, 218, 217

[56] References Cited

U.S. PATENT DOCUMENTS 5,071,875  12/1991  Horn et al. ........................ 514/613
5,276,051  1/1994  Lesieur et al. ...................... 514/415

FOREIGN PATENT DOCUMENTS

| 48729/93 | 4/1994 | Australia . |
| 0763738 | 8/1971 | Belgium ................. 514/628 |
| 2640970 | 12/1988 | France . |
| WO94/07487 | 4/1994 | WIPO . |

OTHER PUBLICATIONS

Arendt, et al., "Alleviation of Jet Lag by Melatonin: Preliminary Results of Controlled Double Blind Trial", *Br. Med. J.*,292: 1170 (1986).

Cassone, et al., "Dose–Dependent Entrainment of Rat Circadian Rhythms by Daily Injection of Melatonin", *J. Biol. Rhythms*, 1: 219–229 (1986).

*Primary Examiner*—Shailendra Kumar
*Attorney, Agent, or Firm*—Sandra M. Nolan

[57] ABSTRACT

Certain N-acyl-cycloalkylamine derivatives are useful as melatonergic agents.

12 Claims, No Drawings

N-ACYL-CYCLOALKYLAMINE DERIVATIVES AS MELATONERGICS

BACKGROUND OF THE INVENTION

The invention pertains to novel N-acyl cycloalkylmethylamine derivatives having drug and bio-affecting properties and to their preparation, pharmaceutical formulations containing them and methods of use. These compounds possess melatonergic properties that should make them useful in treating certain medical disorders.

Melatonin (i; N-acetyl-5-methoxytryptamine) is a hormone which is synthesized and secreted primarily by the pineal gland. In mammals, melatonin levels show a cyclical, circadian pattern, with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

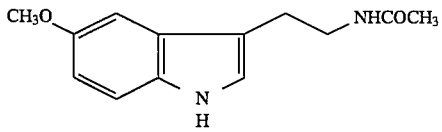
i

Recent evidence demonstrates that melatonin exerts its biological effects through specific receptors. Use of the biologically active, radiolabelled agonist [$^{125}$I]-2-iodomelatonin has led to the identification of high affinity melatonin receptors in the central nervous systems (CNS) of a variety of species. The sequence of one such high affinity melatonin receptor, cloned from frog melanocytes, has been reported. In mammalian brain, autoradiographic studies have localized the distribution of melatonin receptors to a few specific structures.

Although there are significant differences in melatonin receptor distribution even between closely related species, in general the highest binding site density occurs in discrete nuclei of the hypothalamus. In humans, specific [$^{125}$I]-2-iodomelatonin binding within the hypothalamus is completely localized to the suprachiasmatic nucleus, strongly suggesting the melatonin receptors are located within the human biological dock.

Exogenous melatonin administration has been found to synchronize circadian rhythms in rats (Cassone, et al., *J. Biol. Rhythms*, 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487.

Melatonin binding sites have been found in several diverse tissues of the body—i.e., in the retina, superchiasmatic nucleus, spleen, etc. Thus, melatonin exerts multiple physiological effects, is not highly selective, and its potential for producing side effects is significant. Melatonin agonists should be more selective than melatonin and give fewer side effects.

In addition, melatonin's metabolic profile can be problematic in that the compound degrades rapidly in vivo and its oral bioavailability is often low and variable. Suitable melatonin agonists could overcome these drawbacks, resulting in products having more predictability activity.

Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, work-shift syndrome, sleep disorders, glaucoma, reproduction, cancer, immune disorders, neuroendorine disorders, and a variety of sleep disorders.

Aside from simple indole derivatives of melatonin itself, various amide structures have been prepared and their use as melatonin ligands disclosed. In general these amide structures can be represented as:

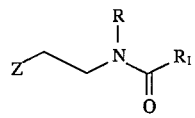
ii wherein Z is an aryl or heteroaryl system attached by a two carbon chain to the amide group. Some specific examples follow.

Yous, et al. in European Patent Application EPA 527 687A disclose as melatonin ligands arylethylamines 1,

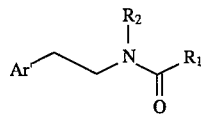
1 wherein Ar' is, inter alia, a substituted or unsubstituted benzo[b]thiophen-3-yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

Horn and Dubocovich in European Patent Application EPA 420 064A disclose 2-amidotetralins 2 as melatonin ligands,

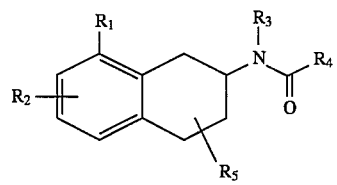
2 wherein $R_1$ is, inter alia, hydrogen, lower alkyl, or lower alkoxyl; $R_2$ is, inter alia, hydrogen, halogen, or lower alkoxyl; $R_3$ is, inter alia, hydrogen, or lower alkyl; $R_4$ is, inter alia, lower alkyl, haloalkyl or cycloalkyl; and $R_5$ is hydrogen, hydroxyl, halogen, oxo, aryl, lower alkyl or alkylaryl.

Langlois, et al., in Australian Patent Application AU-A-48729/93 disclose arylalkyl(thio)amides 3 as melatonergic ligands,

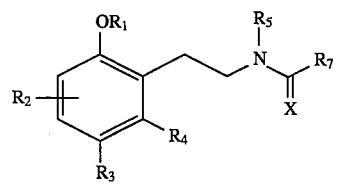
3 wherein $R_1$ is hydrogen or lower alkyl; $R_2$ is hydrogen, halogen, or lower alkyl; $R_3$ and $R_4$ are identical or different groups including, inter alia, hydrogen, halogen, or lower alkyl; $R_5$ is hydrogen or lower alkyl; X is sulfur or oxygen and $R_7$ is, inter alia, lower alkyl or alkenyl.

Bounnaud, et al. in FR 2640970 disclose 1-aryl-2-aminomethylcyclopropane carboxamides of type 4 as antidepressants and anxiolytics,

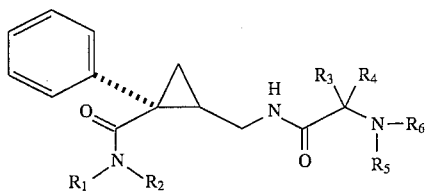

wherein $R_1$ and $R_2$ are lower alkyl; $R_3$ is hydrogen, alkyl, aralkyl or heteroaralkyl; $R_4$, $R_5$, and $R_6$ are independently hydrogen or alkyl.

However these disclosures do not teach or suggest the novel melatonergic compounds of the present invention.

SUMMARY AND DETAILED DESCRIPTION OF THE INVENTION

The present invention is concerned with compounds of Formula I, which possess melatonergic properties and thus have utility in the treatment of conditions affected by melatonin activity.

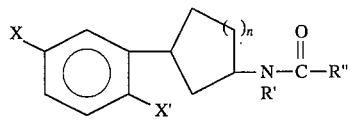

In Formula I, X is halogen to $OR_5$ wherein $R_5$ is $C_{1-20}$ alkyl, $C_{3-20}$ alkenyl, $C_{3-20}$ alkynyl, $C_{9-20}$ aralkyl, $C_{9-20}$ aralkenyl or $C_{9-20}$ aralkynyl; X' is hydrogen or halogen; n is an integer from 0 to 3; R' is hydrogen, $C_{1-4}$ alkyl or benzyl; R" is $C_{1-6}$ alkyl, $C_{2-6}$ alkenyl, $C_{3-6}$ cycloalkyl, $C_{2-4}$ alkoxyalkyl, $C_{2-8}$ alkylthioalkyl or $NR_3R_4$ wherein $R_3$ and $R_4$ are independently selected from hydrogen and $C_{1-4}$ alkyl, but $R_3$ and $R_4$ cannot both be hydrogen.

It is to be understood that, as used herein, "halogen" denotes fluorine, chlorine, bromine and iodine; the term "alkyl" refers to straight and branched chain saturated hydrocarbon radicals; "alkenyl" refers to straight and branched hydrocarbon radicals containing a carbon-carbon double bond; "cycloalkyl" means saturated cyclic hydrocarbon radicals; "alkoxy" denotes an alkyl radical connected to a molecule via an oxygen atom; "alkylthioalkyl" refers to an alkyl radical linked to another via a sulfur atom; "alkynyl" refers to straight and branched hydrocarbon radicals containing a carbon-carbon triple bond; "aralkyl", "aralkenyl", and "aralkynyl" refer to radicals in which an optionally substituted phenyl group is appended to the terminal carbon of an alkyl, alkenyl or alkynyl radical respectively. Phenyl groups, when present, bear substituents selected from hydrogen, halogen and $C_{1-4}$ alkoxy moieties.

Numbers recited in subscripts immediately following "C" denote the number of carbon atoms in the moiety.

Based upon biological tests the following Formula I compounds are preferred. All have activities of 250 nM or less at the human melatonin receptor.

Preferred compounds of formula I are those wherein X is $OR_5$, wherein $R_5$ is $C_{1-4}$ alkyl; X" is hydrogen; n is 1 or 2; R' is hydrogen and R" is $C_{1-4}$ alkyl. It is preferred that R" contain no nitrogen, oxygen or sulfur atoms.

Preferred compounds of the present invention include:
(cis)-N-[3-Methoxyphenyl)cyclohexyl]acetamide;
(cis)-N-[3-Methoxyphenyl)cyclohexyl]-2-methyl-propanamide;
(cis)-N-[3-Methoxyphenyl)cyclohexyl]butanamide;
(cis)-N-Ethyl-N'-[3-methoxyphenyl)cyclohexyl]urea; and
N-[3-Methoxyphenyl)cyclopentyl]butanamide.

Reagents, solvents and reaction conditions for the above described preparative steps would be known to one skilled in the art of organic synthesis. All the steps are standard organic reactions having extensive precedent in the scientific literature.

These preparative methods may be varied in order to produce other compounds embraced by this invention but not specifically disclosed.

Additionally compounds of Formula I also encompass all pharmaceutically acceptable solvates, hydrates being the preferred solvates. The present invention also includes both geometrical isomers as well as optical isomers, e.g. mixtures of enantiomers as well as individual enantiomers and diastereomers, which arise as a consequence of structural asymmetry in certain compounds of the instant series. Cis-isomers are the preferred isomers. Separation or stereospecific synthesis of the individual isomers is accomplished by application of various methods which are well known to practitioners in the art.

The compounds of the present invention have affinity for receptors of the endogenous pineal hormone, melatonin, as determined in a receptor binding assay, and exhibit agonist activity as determined by a functional assay; the biological tests are described hereinbelow. As has been discussed above, melatonin is involved in the regulation of a variety of biological rhythms and exerts its biological effects via interaction with specific receptors. There is evidence that administration of melatonin agonists are of clinical utility in the treatment of various conditions regulated by melatonin activity. Such conditions include depression, jet-lag, work-shift syndrome, sleep disorders, glaucoma, some disorders associated with reproduction, cancer, immune disorders and neuroendocrine disorders.

The systemic administration and dosing regimen of compounds of Formula I can be considered to be done in a manner similar to that described for melatonin itself. The dosage and dosage regimen must be adjusted using sound professional judgment and taking into consideration such variables as the age, body weight, sex and physical condition of the recipient, the route of administration and the nature of the illness being treated. Oral, transdermal, subcutaneous, intravenous, intramuscular, rectal, buccal, intranasal, and ocular routes of administration may be used.

One or more of the compounds of the invention is mixed with pharmaceutically acceptable amounts of one or more conventional pharmaceutical excipients to produce a formulation to be administered by the desired route. Generally, such formulations will contain one or several carriers or diluents. Useful carriers include solids, semi-solids and liquids which have miscibility, or other compatability, with the active agent(s) so that they can deliver same to a patient or host.

Suitable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate, mineral oil and the like. Mixures are operable.

Other useful excipients include lubricants, wetting agents, gellants, emulsifiers, preservatives, colorants, perfumes, flavor enhancers, drying agents and the like. Mixtures can be employed.

Generally, compositions which include the compounds of the invention will contain from about 0.10 to about 10% of active compound(s) and 99.9 to 90%, or other suitable amounts, of excipient(s).

Dosage levels will be dictated by the patient's needs and by the medical judgment of the treating physician. Generally, however, dosages of about 0.1 mg to about 100 mg per day are useful to treat sleep, circadian rhythm or other medical disorders.

In methods of treatment employing the compounds of the invention, the treatment will involve the step(s) of administering one or more dosages of the compound to a host, preferably a mammalian, e.g. human host in need of such treatment.

DESCRIPTION OF SPECIFIC EMBODIMENTS

The compounds which constitute the present invention, their methods of preparation and their biological actions will appear more fully after consideration of the following examples, which are given for the purpose of illustration only and are not to be construed as limiting the invention's scope.

In the following examples, temperatures are expressed in degrees Celsius (°C.), hours are designated "h" or "hr", and melting points are uncorrected. The proton nuclear magnetic resonance (NMR) spectral characteristics refer to chemical shifts (δ) expressed as parts per million (ppm) versus tetramethylsilane (TMS) as the reference standard. The relative area reported for NMR signals at various chemical shifts corresponds to the number of hydrogen atoms of a particular type in the molecule. The multiplicities of the signals are reported as broad singlet (br s), singlet (s), doublet (d), triplet (t) or multiplet (m). The NMR spectra were obtained using solutions of the compounds in either deuterodimethylsulfoxide (DMSO-$d_6$) or deuterochloroform (CDCl$_3$). Infrared (IR) spectral descriptions include only absorption wave numbers (cm−1) having functional group identification value and IR determinations were made using potassium bromide (KBr) as diluent. The elemental analyses are reported as percent by weight.

The following examples describe the preparation of representative examples of compounds of Formula I and of synthetic intermediates. There is also a description of the melatonergic binding test used. It will be apparent to those skilled in the art that modifications, both of material and methods, will allow preparation of other compounds disclosed herein. From the foregoing description and the following examples it is believed that one skilled in the art is able to carry out the invention to the fullest extent.

EXAMPLES

The compounds of Formula I were prepared by the method shown in Scheme 1. An organometallic reagent (1), such as a Grignard reagent or an aryl lithium reagent, is condensed with the appropriate cycloalkenone (2) in the presence of a copper(I) salt such as CuBr, CuI, CuBr·Me$_2$S, or the like, to give the 3-aryl-cycloalkanone (3) directly. Alternatively, 1 can be condensed with a 3-alkoxy-cycloalkenone (4), which gives 3 after subsequent ketalization, catalytic hydrogenation, and deprotection steps. Suitable catalysts for this conversion include palladium on carbon, and the like. Cycloalkanone, 3, can be converted to the compounds of Formula I by standard methods, such as condensation with hydroxyamine, followed by catalytic hydrogenation, and subsequent acylation. Suitable catalysts for this conversion include Raney Nickel, palladium on carbon, and the like. Suitable acylating agents include carboxylic acid halides, anhydrides, acyl imidazoles, alkyl isocyanates, and carboxylic acids in the presence of condensing agents, such as carbonyl imidazole, carbodiimides, and the like.

Scheme 1:

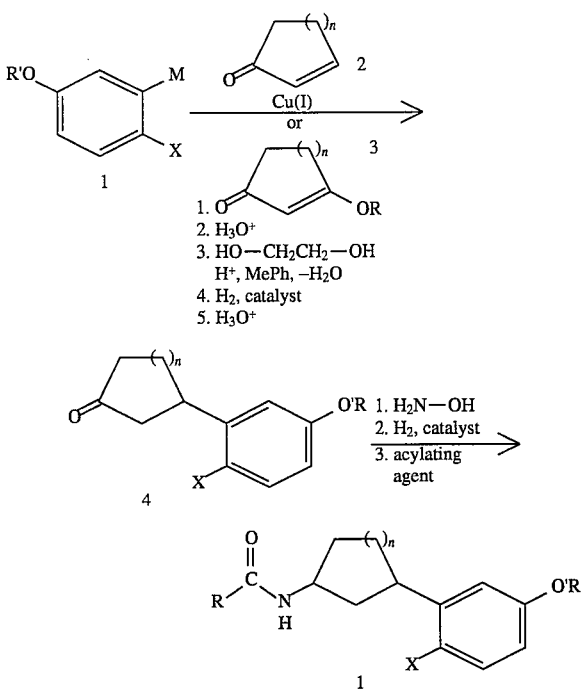

Preparation of Compounds of Formula I from a 2-cycloalkenone:

Example 1

Mixture of cis- and trans-N-[3-(3-methoxyphenyl)-cyclopentyl]butanamide

A solution of 2-cyclopentenone (8.21 g, 0.1 mol) in THF (50 ml) was added dropwise to the Grignard reagent formed from 3-bromo anisole (18.7 g, 0.1 mol) and magnesium metal (2.5 g) in THF (200 ml). The solution was stirred for 18 hr, and then quenched with the slow addition of 3N HCl (75 ml). The mixture was stirred for 1 hr and diluted with ethyl ether (200 ml). The organic layer was separated, extracted twice with water, and twice with brine. The organic solution was then concentrated to an amber oil that was chromatographed on silica gel using CH$_2$Cl$_2$/hexanes mixture as the eluent to give the desired cyclopentanone (2.0 g, 10.5%, IR: 1734 cm$^{-1}$).

A solution of the above cyclopentanone (1.9 g, 10 mmol), hydroxylamine hydrochloride (2.8 g, 40 mmol), and sodium hydroxide (4 ml of 10N, 40 mmol) in ethanol (150 ml), was refluxed for 18 hr. The mixture was cooled and then hydrogenated at 60 psi for 4 hr over Raney nickel (4 g). The mixture was filtered and the filtrate was concentrated in vacuo. The residue was dissolved in acetonitrile (100 ml) and HCl (2 ml of 12N), and the solution was concentrated in vacuo. The residue was triturated with acetonitrile to give a gummy solid that recrystallized from ethanol to give the amine hydrochloride a white powder (0.5 g, 26.2%).

A solution of the amine salt intermediate (0.5 g, 2.62 mmol) in pyridine (10 ml) was cooled in an ice bath as butyryl chloride (0.363 ml, 3.5 mmol) was added. The reaction mixture was stirred for 4 hr at room temperature, and then concentrated. The residue was dissolved in methylene chloride (50 ml) and extracted twice with 1N HCl (30 ml). The organic layer was concentrated and the crude product was chromatographed on silica gel using methylene chloride/ethyl acetate as the eluent to give a mixture of cis- and trans-N-[3-(3-methoxyphenyl)-cyclopentyl]-butanamide as a clear oil (0.3 g, 43.8%). Calc'd for $C_{16}H_{23}NO_3$: C, 74.53; H, 8.87; N, 5.36. Found: C, 73.18; H, 8.79; N, 5.36. MS (isobutane-DCI): 262 (M+H). IR (film): 3288, 2960, 1638, 1548, 1264, 698 $cm^{-1}$.

Preparation of Compounds of Formula I from a 3-alkoxy-cycloalkenone:

Example 2

(cis)-N-[3-(3-Methoxyphenyl)cydohexyl]butanamide

A solution of 3-(2-propyloxy)-2-cyclohexenone (28.0 g, 0.182 mol) in THF (100 ml) was added dropwise to the Grignard reagent formed from 3-bromo-anisole (37.4 g, 0.2 mol) and magnesium metal (6.08 g, 0.25 mol) in THF (400 ml). The solution was stirred for 3 hr, and then quenched with the slow addition of 3N HCl (150 ml). The mixture was stirred for 16 hr and diluted with ethyl ether (400 ml). The organic layer was separated, extracted twice with water (100 ml), and twice with brine. The organic solution was then concentrated to an amber oil that was Kügelrohr distilled to give the intermediate enone as a pale amber oil (35.1 g, 95.5%). PMR (CDCl$_3$, 300 MHz): δ2.17 (m, 2H), 2.50 (t, 2H), 2.77 (t, 2H), 3.85 (s, 3H), 6.41 (s, 1H), 6.97 (d of d, 1H), 7.06 (t, 1H), 7.15 (d, 1H), 7.30 (t, 1H). IR (film): 1663 $cm^{-1}$.

A mixture of the above amber oil (35.1 g, 0.174 mol), ethylene glycol (15 g, 0.242 mol), and p-toluene sulfonic acid (0.5 g) in toluene (200 ml) was heated to reflux under a Dean-Stark trap for 18 hr. Another portion of p-toluene sulfonic acid (0.5 g) was added and the heating continued 24 hr. The solution was cooled and extracted twice with saturated sodium carbonate (100 ml), twice with water, and twice with brine. The organic layer was concentrated to a brown oil that was Kügelrohr distilled to give the intermediate ketal as a clear oil that was taken on. PMR (CDCl$_3$, 300 MHz): δ1.85 (t, 2H), 2.4–2.5 (m, 2H), 2.66 (bs, 2H), 3.84 (s, 3H), 4.04 (s, 4H), 6.17 (m, 1H), 6.80 (d of d, 1H), 8.95 (t, 1H), 7.00 (d, 1H), 7.25 (t, 1H).

A solution of the intermediate oil in ethanol (200 ml) was hydrogenated for 18 hr at 60 psi over 10% Pd/C (1 g). The mixture was filtered, and the filtrate was stirred with 3N HCl (75 ml) for 4 hr. The solution was concentrated and extracted three times with ethyl acetate (200 ml). The organic extracts were dried with brine and concentrated. The oily residue was Kügelrohr distilled to the intermediate ketone as a clear oil (29.97 g, 95%). PMR (CDCl$_3$, 300 MHz): δ1.73–1.95 (m, 2H), 2.05–2.2 (m, 2H), 2.33–2.63 (m, 4H), 2.95–3.07 (m, 1H), 3.87 (s, 3H), 6.70–6.85 (overlapping, 3H), 7.20–7.30 (m, 1H). IR (film): 1711 $cm^{-1}$.

A solution of the above ketone (10.86 g, 53.24 mmol) in ethanol (150 ml) was added to a mixture of hydroxylamine sulfate (12.31 g, 0.15 mol) and 10N sodium hydroxide (15 ml) and then heated to reflux for 6 hr. The mixture was cooled and then hydrogenated at 60 psi over Raney nickel (2 g) for 16 hr. The mixture was filtered and the filtrate concentrated to a gummy residue. The residue was partitioned between ethyl acetate and water. The organic layer was separated, extracted twice with water (75 ml), and then three times with 3N HCl (100 ml total). The HCl extracts were made basic with 50% sodium hydroxide, and then extracted three times with ethyl acetate (100 ml). The organic extracts were dried over brine and concentrated. The residue was dissolved in acetonitrile (50 ml) and 12N HCl was added dropwise to give the amine hydrochloride intermediate as a white precipitate that was filtered and air dried (2.54 g, 19.8%).

A solution of the amine salt intermediate (0.53 g, 2.59 mmol) in pyridine (10 ml) was cooled in an ice bath as butyryl chloride (0.33 mL, 3.2 mmol) was added via a syringe. The reaction mixture was stirred for 2 hr at room temperature, and then concentrated. The residue was dissolved in methylene chloride (30 ml) and extracted twice with 1N HCl (30 ml). The organic layer was concentrated and the crude product was chromatographed on silica gel using methylene chloride/ethyl acetate as the eluent to give (±)-cis-N-[3-(3-methoxyphenyl)-cyclohexyl]-butyramide as a clear oil (0.45 g, 62.7%).

Calc'd for $C_{17}H_{25}NO_2 \cdot 0.2\ H_2O$: C, 73.18; H, 9.18; N, 5.02. Found: C, 73.27; H, 9.17; N, 5.01.

MS (isobutane-DCI): 276 (M+H).

IR (film): 3286, 2932, 1640, 1548, 1268, 698 $cm^{-1}$.

CMR (CDCl$_3$): δ13.68, 19.25, 25.05, 32.93, 32.98, 38.93, 41.10, 43.12, 48.43, 55.12, 111.18, 112.70, 119.11, 129.31, 147.87, 159.60, 171.98 ppm.

Example 3

(±)-cis-N-[3-(3-methoxyphenyl)-cyclohexyl]-2-methyl-propanamide

This compound was prepared in a manner similar to that given in Example 2, and was isolated as a white powder (0.49 g, 68.3%, mp: 89°–92° C.). Calc'd for $C_{17}H_{25}NO_2 \cdot 0.09\ H_2O$: C, 73.71; H, 9.16; N, 5.06. Found: C, 73.78; H, 9.16; N, 5.01.

MS (isobutane-DCI): 276 (M+H).

IR (film): 3290, 2930, 1642, 1544, 1236, 698 $cm^{-1}$.

CMR (CDCl$_3$): δ19.60, 19.67, 25.08, 32.91, 32.96, 35.78, 41.17, 43.16, 48.31, 55.15, 111.23, 112.73, 119.14, 129.33, 147.91, 159.66, 175.97 ppm.

Example 4

(±)-cis-N-[3-(3-methoxyphenyl)cyclohexyl]acetamide

This compound was prepared in a manner similar to that given in Example 2, and was isolated as a dear oil (0.25 g, 38.8%). Calc'd for $C_{15}H_{21}NO_2 \cdot 0.1\ H_2O$: C, 72.29; H, 8.59; N, 5.60. Found: C, 72.31; H, 8.58; N, 5.62.

MS (isobutane-DCI): 248 (M+H).

IR (film): 3284, 2932, 1652, 1554, 1270, 698 $cm^{-1}$.

CMR (CDCl$_3$): δ23.56, 25.07, 32.93, 33.01, 40.95, 43.12, 48.71, 55.15, 111.23, 112.73, 119.13, 129.34, 147.84, 159.65, 169.08 ppm.

Example 5

(cis)-N-Ethyl-N'-[3-(3-methoxyphenyl)cyclohexyl]urea

This compound was prepared in a manner similar to that given in Example 2, and was isolated as a clear oil (0.36 g, 49.2%). Calc'd for $C_{16}H_{24}N_2O_2 \cdot 0.35\ H_2O$: C, 67.98; H, 8.81; N, 9.91. Found: C, 67.92; H, 9.01; N, 9.99.

MS (isobutane-DCI): 277 (M+H).

IR (film): 2930, 1632, 1570, 1268, 1156, 1048 $cm^{-1}$.

CMR (CDCl$_3$): δ15.39, 25.15, 33.07, 33.58, 35.35, 41.61, 43.25, 49.67, 55.12, 111.13, 112.13, 119.13, 129.30, 147.93, 157.67, 159.58 ppm.

Example 6

Measurement of Melatonergic Binding

The melatonergic binding of the compounds of Formula I was determined by the method of Reppert, S. M., Weaver, D. R., and Ebisawa, R. (*Neuron*, Volume 13, pages 1177–1185, 1994). The assays were incubated at 37° C. for 1 hour, and the reaction was terminated by filtration through a Brandel cell harvester. The filters were washed 3 times with wash buffer. While compounds with $IC_{50}$ values less than 250 nM are termed active, compounds made in Examples 1–5 possess $IC_{50}$ values less than 30 nM. The reagents, membranes, and techniques used in the melatonergic binding assays are more fully described below:

1. Reagents
   (a) 50 mM Tris buffer containing 12.5 mM $MgCl_2$ and 2 mM EDTA (pH 7.4 at 37° C.).
   (b) Wash buffer: 20 mM Tris base containing 2 mM $MgCl_2$ (pH 7.4 at room temperature).
   (c) 6-Chloromelatonin ($10^{-5}$M final concn.).
   (d) 2-[$^{125}$I]-Iodomelatonin (100 pM final concn.). Source: NEN
2. Membrane preparation. The cDNA (human $ML_{1A}$) was introduced into COS-1 cells by the DEAE-dextran method. Three days later, the media was removed, the plates washed with phosphate buffered saline, the cells removed using Hank's balanced salt solution and pelleted. The supernatant was discarded and the pellets frozen. For preparing membrane homogenates, the pellets are thawed on ice, and resuspended in TME buffer, Tris base, $MgCl_2$, EDTA (pH 7.4 at 37° C.), supplemented with aprotinin, leupeptin and phenylmethylsulfonylfluoride. The cells were then homogenized using a dounce homogenizer and centrifuged. The resulting pellet was resuspended with a dounce homogenizer in TME and frozen. On the day of assay, a small aliquot was thawed on ice and resuspended in TME buffer (1:1000).

Reasonable variations, such as those which would occur to a skilled artisan, can be made herein without departing from the scope of the invention.

We claim:

1. A melatonergic compound of Formula I

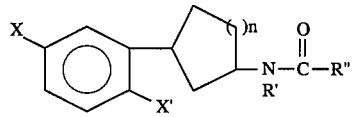

(I)

wherein:

X is halogen or $OR_5$ wherein $R_5$ is $C_{1-20}$ alkyl, $C_{3-20}$ alkenyl, $C_{3-20}$ alkynyl, $C_{9-20}$ aralkyl, $C_{9-20}$ aralkenyl or $C_{9-20}$ aralkynyl;

X' is hydrogen or halogen;

n is an integer from 0 to 3;

R' is hydrogen, $C_{1-4}$ alkyl or benzyl; and

R" is $C_{1-6}$ alkyl, $C_{2-6}$ alkenyl, $C_{3-6}$ cycloalkyl, $C_{2-4}$ alkoxyalkyl or $C_{2-4}$ alkylthioalkyl.

2. The compound of claim 1 wherein R' is hydrogen and R" contains no nitrogen, oxygen or sulfur atoms.

3. The compound of claim 2 wherein R" is $C_{1-4}$ alkyl.

4. The compound of claim 3 wherein X" is hydrogen.

5. The compound of claim 4 wherein X is $OR_5$ and $R_5$ is methyl.

6. The compound of claim 5 selected from the group consisting of:
(cis)-N-[3-(3-methoxyphenyl)cyclohexyl]acetamide;
(cis)-N-[3-(3-methoxyphenyl)cyclohexyl]-2-methyl-propanamide;
(cis)-N-[3-(3-methoxyphenyl)cyclohexyl]butanamide; and
N-[3-(3-methoxyphenyl)cyclopentyl]butanamide.

7. The compound of claim 1, (cis)-N-[3-(3-methoxyphenyl)cyclohexyl]acetamide.

8. The compound of claim 1, (cis)-N-[3-(3-methoxyphenyl)cyclohexyl]-2-methyl-propanamide.

9. The compound of claim 1, (cis)-N-[3-(3-methoxyphenyl)cyclohexyl]butanamide.

10. The compound of claim 1, N-[3-(3-methoxyphenyl)cyclopentyl]butanamide.

11. A method of treating a circadian rhythm-related disorder in a patient in need of such treatment comprising administering to said patient a therapeutic amount of a compound of claim 1.

12. A pharmaceutical composition for treating circadian rhythm-related disorders comprising a suitable amount of a pharmaceutically acceptable carrier and a therapeutic amount of a compound of claim 1.

* * * * *